United States Patent
Mechlenburg et al.

(10) Patent No.: US 6,564,797 B1
(45) Date of Patent: May 20, 2003

(54) INTERACTIVE PRESSURE SUPPORT SYSTEM AND METHOD

(75) Inventors: Douglas M. Mechlenburg, Pittsburgh, PA (US); Mark C. Estes, Sylmar, CA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/399,023

(22) Filed: Sep. 20, 1999

Related U.S. Application Data

(60) Provisional application No. 60/102,468, filed on Sep. 30, 1998.

(51) Int. Cl.[7] ............................................. A61M 16/00
(52) U.S. Cl. ............................ 128/204.21; 128/204.18; 128/204.23
(58) Field of Search ..................... 128/204.18, 204.21, 128/905, 204.23; 600/529, 532, 543; 434/262

(56) References Cited

U.S. PATENT DOCUMENTS

| | | | | | |
|---|---|---|---|---|---|
| 4,957,107 A | * | 9/1990 | Sipin | ..................... | 128/204.21 |
| 4,984,158 A | * | 1/1991 | Hillsman | ............... | 128/200.14 |
| 5,167,506 A | * | 12/1992 | Kilis et al. | ............. | 128/200.14 |
| 5,363,842 A | * | 11/1994 | Mishelevich et al. | .. | 128/200.14 |
| 5,433,193 A | * | 7/1995 | Sanders et al. | ........ | 128/204.18 |
| 5,537,997 A | * | 7/1996 | Mechlenburg et al. | . | 128/204.23 |
| 5,540,219 A | * | 7/1996 | Mechlenburg et al. | . | 128/204.23 |
| 5,645,054 A | * | 7/1997 | Cotner et al. | .......... | 128/204.23 |
| 5,692,497 A | * | 12/1997 | Schnitzer et al. | ...... | 128/204.21 |
| 5,704,345 A | * | 1/1998 | Berthon-Jones | ........ | 128/204.23 |
| 5,881,723 A | * | 3/1999 | Wallace et al. | ......... | 128/204.21 |
| 5,913,310 A | * | 6/1999 | Brown | ....................... | 128/897 |
| 5,927,274 A | * | 7/1999 | Servidio et al. | ....... | 128/204.18 |
| 5,931,160 A | * | 8/1999 | Gilmore et al. | ........ | 128/204.21 |
| 5,954,050 A | * | 9/1999 | Christopher | ........... | 128/204.23 |
| 6,083,007 A | * | 7/2000 | Joliat et al. | .................. | 434/262 |
| 6,085,752 A | * | 7/2000 | Kehr et al. | .................. | 128/897 |
| 6,158,432 A | * | 12/2000 | Biondi et al. | .......... | 128/204.21 |
| 6,190,326 B1 | * | 2/2001 | McKinnon et al. | ..... | 128/200.24 |
| 6,367,475 B1 | * | 4/2002 | Kofoed et al. | ......... | 128/200.24 |
| 6,398,739 B1 | * | 6/2002 | Sullivan et al. | ........ | 128/204.18 |
| 6,419,629 B1 | * | 7/2002 | Balkin et al. | ............... | 600/300 |

OTHER PUBLICATIONS

Product Brochure entitled, "Virtuoso LX Smart CPAP System", Respironics, Inc. 1997.

Hirshkowitz et al., "The Multiple Vigilance Test", 1993, Behavior Research Methods, Instruments, and Computers, vol. 25 No. 2, 272–275.

Johns, "Sleepiness in Different Situations Measured by the Epworth Sleepiness Scale", 1994, Sleep, vol. 17, No. 8, 703–710.

* cited by examiner

Primary Examiner—Weilun Lo
Assistant Examiner—Mital Patel
(74) Attorney, Agent, or Firm—Michael W. Haas

(57) ABSTRACT

An interactive pressure support system and method employing a pressure generating system that provides a pressure therapy to the pulmonary system of a patient and an interactive system associated with the pressure generating system to enable the patient to interact with the pressure support system, for example, to monitor the effectiveness of the treatment provided by the pressure support system. The interactive system includes an output device that provides first information to the patient, an input device that allows the patient to provide second information that is based on the first information and a control unit that controls the operation of the output device to present the first information and collection of the second information via the input device.

21 Claims, 2 Drawing Sheets

INTERACTIVE PRESSURE SUPPORT SYSTEM AND METHOD

CROSS-REFERENCE TO RELATED APPLICATIONS

This application claims priority under 35 U.S.C. §119(e) from provisional U.S. patent application No. 60/102,468 filed Sep. 30, 1998.

BACKGROUND OF THE INVENTION

1. Field of the Invention

The present invention pertains to an interactive pressure support system and to a method of treating a breathing disorder using same, and, in particular, to a system that provides a pressure therapy to a patient while also providing an interactive capability so that the patient can answer questions or perform tasks that ascertain the effectiveness of the pressure therapy in treating the patient's breathing disorder.

2. Description of the Related Art

There are many medical ailments that are diagnosed and/or monitored using a questionnaire or cognitive test taken by the patient. For example, a common method to determine whether a patient suffers from a sleep disorder, such as obstructive sleep apnea (OSA), is to measure the patient's sleep propensity. The patient's sleep propensity and/or changes in the sleep propensity can also be used to determine the severity of the disorder and/or monitor the changes in the patient's condition. One conventional technique for measuring a patient's sleep propensity is through the use of the Epworth Sleepiness Score (ESS). The ESS is determined based on the patient's retrospective reports of dozing behavior in a variety of situations commonly encountered in normal daily life. These retrospective reports are elucidated from the patient via a series of questions. The patient's responses to these questions are tabulated and used to determine the ESS to evaluate his or her sleep propensity.

Currently, the Epworth Test is typically administered on paper. To do so, the written test must be physically supplied to the patient and collected after the patient completes the questions. The test administrator manually tabulates (or uses a computer to tabulate) the responses provided by the patient and calculates the ESS based on the patient's responses. It can be appreciated that the administrative requirements, such as the distribution, collection, time stamping, tabulation, scoring, storing and record keeping, required by this conventional testing technique place a significant burden on the test givers. This burden increases with the number of patient's taking the test as well as the number of times the test is administered to each patient. Typically the same patient will take the Epworth test multiple times during his or her treatment in order to monitor the effectiveness of the treatment therapy. It can thus be appreciated that patient follow-up to determine, for example, the effectiveness of a therapy intended to treat a sleep or breathing disorder, is a relatively expensive and burdensome process.

Another conventional technique that measures a patient's reaction time and cognitive alertness, which are generally understood to be indicative of a patient's sleep propensity, is the Vigilance test. This test is typically administered using a personal computer (PC) and requires that the patient provide responses via the input devices associated with the PC to displayed indicia. The patient's reaction time in providing the response and/or the accuracy of the response to the displayed indicia are measured and stored to determine the patient's level of alertness. For example, the patient is shown a recognizable object on the PC display, and the patient's reaction time in identifying the object and the accuracy of the identification are measured.

Because this test typically requires a PC to administer, it can only be administered at a facility where an appropriately programmed PC is located, which requires that the patient travel to a place where such a PC is located. Alternatively, an appropriately programmed PC can be provided to the patient. However, this latter alternative represents a significant cost in furnishing the PC to the patient and requires training the patient on the use of such a relatively complicated device. It can thus be appreciated that either alternative for administering the Vigilance test represents a significant burden on either the patient or the test administrator.

SUMMARY OF THE INVENTION

Accordingly, it is an object of the present invention to provide a device and method for providing a pressure support treatment and for administering a questionnaire or cognitive test to a patient that overcomes the shortcomings of conventional techniques. This object is achieved, according to one embodiment of the present invention, by providing an interactive pressure support system that includes a pressure generating system adapted to provide a pressure therapy to a pulmonary system of a patient and an interactive system associated with the pressure generating system. The interactive system includes an output device that provides information, such as questions or symbols, to the patient and an input device that receives information from the patient, such as responses to the questions or reactions to the symbols presented. The interactive system also includes a control unit that controls the operation of the output device and the input device to present the interrogative information to the patient properly and to collect the responses from the patient provided via the input device.

This single system combines the patient therapy function of the pressure support device with the patient evaluation function of the questionnaire or cognitive test administered by the interactive system. This dual function system reduces the administrative burden and costs of providing the questionnaire or cognitive test because the test is performed using the same device the patient is given to treat the disorder, and the testing procedure and results collection, calculation, storage, and communication functions are performed in an automated fashion using the processing capabilities already present in many pressure support devices. Furthermore, because the test is incorporated into the same device that the patient is given to treat the condition being monitored by the test, the patient is likely to be motivated to perform the test correctly and diligently, as well as being familiar with the device used to administer the test, thereby requiring less training to perform the testing function than if the patient is provided with an entirely different testing system.

In further embodiments of the present invention, the control unit performs additional functions, such as tabulating the results provided by the patient and calculating scores indicative of the patient's condition, e.g., the ESS indicative of the patient's sleep propensity. In other embodiments, a memory unit is provided that enables the interactive pressure support system to store a number of different types of tests and the results provided by the patient upon taking the tests, including the results from repeated tests and information identifying the time/date the test was administered. In yet another embodiment, a communication unit is provided that permits communication of data between the interactive system and a remote location so that new test data can be provided to the interactive pressure support system and/or information collected by the system can be provided to the remote location, for example.

It is yet another object of the present invention to provide a method of treating and monitoring the treatment of a breathing disorder that does not suffer from the disadvantages of conventional techniques. This object is accomplished by providing a method that includes the steps of: (1) providing a device that administers a pressure therapy to a patient and includes an interactive capability, (2) causing the device to provide information to the patient, such as questions or symbols, and (3) acquiring, via the device, information from the patient, such as responses to the questions or reactions to the symbols presented. In further embodiments of the present invention, the above method also includes storing different information to provide to the patient and storing the results provided by the patient based thereon, as well as the results of repeated testing of the patient. Still other embodiments include the step of communicating with a remote location to exchange information with the interactive pressure support device, such as different or additional test information to provide to the patient and the results provided by the patient based thereon.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
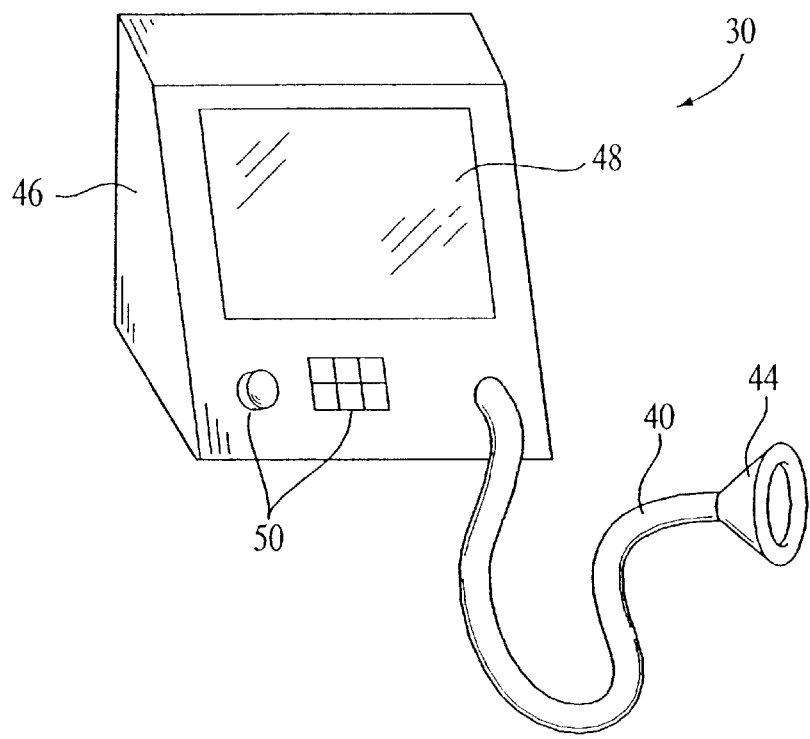
FIG. 1 is a perspective view of an interactive pressure support system according to a first embodiment of the present invention.
Figure 2:
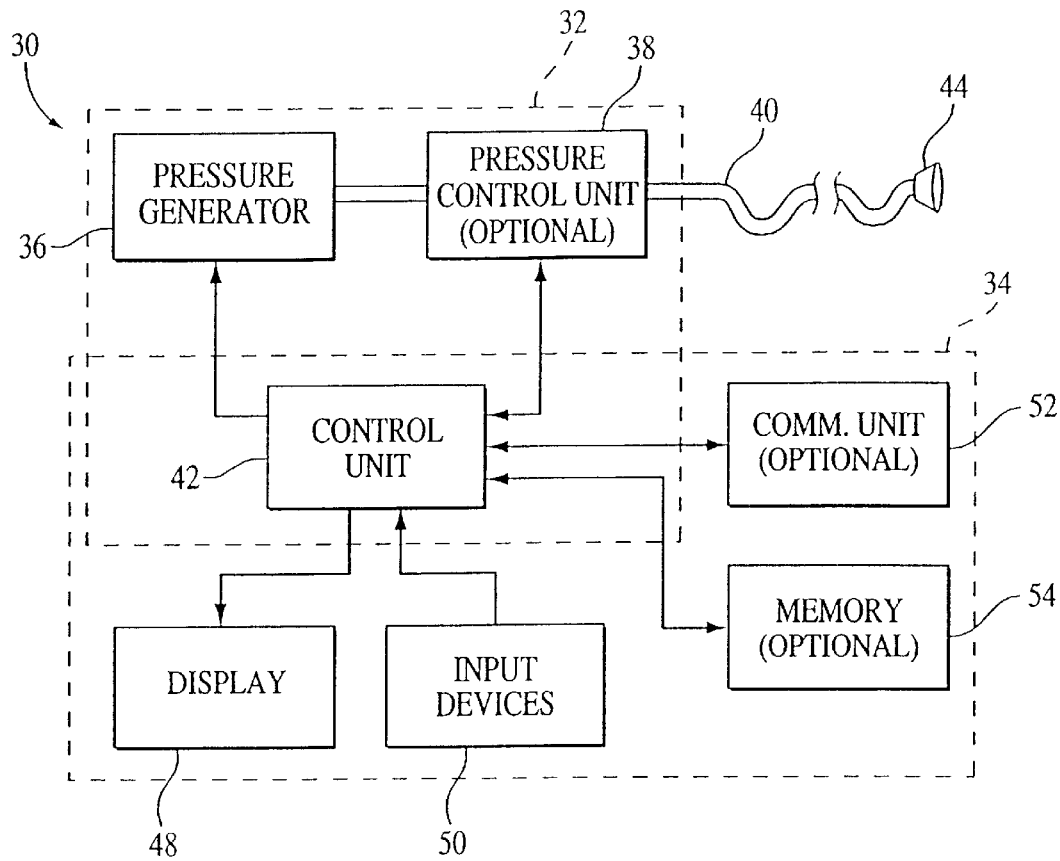
FIG. 2 is a schematic diagram of the interactive pressure support system illustrated in FIG. 1.

FIGS. 1 and 2 illustrate a first embodiment of an interactive pressure support system 30 according to the principles of the present invention. Interactive pressure support system 30 includes two systems; a pressure generating system 32, and an interactive system 34. Pressure generating system 32 provides a positive pressure therapy to a patient. For example, pressure generating system provides a continuous positive airway pressure therapy (CPAP), a variable pressure therapy in which the pressure provided to the patient varies with inspiration and expiration, or a variable pressure therapy in which the pressure provided to the patient varies as necessary to treat the patient's disorder.

In general, pressure generating system 32 includes a pressure generator 36 and, if necessary, a pressure control unit 38. For the least complex type of pressure therapy, such as CPAP, pressure control unit 38 is generally not necessary because the pressure provided to the patient remains constant or follows a predetermined profile regardless of the condition of the patient. For the variable pressure therapies, such as a bi-level therapy, which is taught by U.S. Pat. Nos. 5,148,802 and 5,443,193 both to Sanders et al. and by U.S. Pat. No. 5,313,937 to Zdrojkowski et al., the contents of which are hereby incorporated by reference into the present application, proportional positive airway pressure (PPAP), which is taught by U.S. Pat. Nos. 5,535,738 and 5,794,615 both to Estes et al., the contents of which are hereby incorporated by reference into the present application, and proportional assist ventilation (a.k.a. PAV), which is taught by U.S. Pat. Nos. 5,044,362 and 5,170,830, both to Younes, the contents of which are also hereby incorporated by reference into the present application, pressure control unit 38 controls the pressure provided to the patient. Typically pressure control unit 38 controls the pressure to the patient by regulating the pressure in a patient delivery circuit 40 that delivers the gas to the patient via a valve or series of valves or by controlling the output of the pressure generator, such as the speed of the blower, in a blower-based pressure generator.

The variable pressure therapy systems include a sensor (not shown) that detects the conditions of the patient so that the pressure provided to the patient can be controlled based on the detected condition. For example, if the pressure provided to the patient varies with the patient's breathing cycle, a sensor, such as a flow or pressure sensor associated with breathing circuit 40, is provided to detect changes in the breathing cycle, such as changes from inspiration to expiration and vise versa. The pressure/flow delivered to the patient is controlled by the pressure control unit to vary depending on whether the patient is inhaling or exhaling.

If the pressure provided to the patient changes with changes necessary to treat the patient's disorder, a sensor is used to monitor the disorder. For example, a flow and/or pressure sensor coupled to the breathing circuit detects aberrations in the flow of gas to and from the patient, or a microphone or pressure sensor detects snoring, both of which are generally indicative of an obstruction in the patient's airway. The pressure control unit controls the pressure provided to the patient based on the feedback from these sensors to provide enough pressure to alleviate the disorder, such as the airway obstruction, while reducing the pressure once the disorder abates. U.S. Pat. Nos. 5,203,343 and 5,458,137 both to Axe et al. and U.S. Pat. No. 5,645,053 to Remmers et al., the contents of which are incorporated herein by reference, are examples of pressure support systems in which the pressure provided to the patient changes with changes necessary to treat the patient's disorder.

In the illustrated embodiment, a control unit 42 cooperates with pressure generator 36 and pressure control unit 38 to control the operation of pressure generating system 32. According to one embodiment of the present invention, control unit 42 performs the patient monitoring function and controls the pressure provided to the patient as discussed above in conjunction with pressure control unit 38. It can be appreciated, however, that control unit 42 can perform other functions, such as monitoring use of the pressure generating system (patient compliance), running diagnostic routines and providing error/warning indications. Also, a patient interface device 44, such as a nasal mask, nasal/oral mask, total face mask, nasal cannula, trachea tube, or any other suitable device connects the patient to breathing circuit 40.

Interactive system 34 provides an interactive capability that augments the pressure therapy function of pressure generating system 32. Interactive system 34 enables the system to query the patient about his or her condition and/or have the patient perform tasks that provide an indication of the patient's condition. In the illustrated embodiment, interactive system 34 shares a common housing 46 with pressure generating system 32. This provides an advantage in that the same device that is used to treat the patient's disorder, i.e., the device containing the system that provides the pressure therapy, also can be used to administer a questionnaire or cognitive test, thereby avoiding the need to have the patient travel to a test location or to have the test administrator manually distribute and administer a paper test each time the patient is or needs to be tested. This combination also takes advantage of the processing facilities commonly included in current pressure support devices, thereby minimizing the cost of including or retrofitting the interactive function on current pressure support devices.

Interactive system 34 includes an output device 48, which, in the illustrated embodiment, is a display, and an input device 50, both of which are operatively coupled to control unit 42. Display 48 is used to provide questions, symbols, pictures, or other visible indicia to the user. Display 48 can be any suitable display device, such as an LCD or cathode ray tube. It is to be understood, however, that other output devices are contemplated by the present invention. For example, the output device can be an audio or Braille device for the visually impaired, a printer, or any device that outputs information from the interactive system in a form perceivable to the user. Input device 50 is used to provide information from the user to the control unit. Input device 50 can be any suitable device, such as a keyboard, keypad, touch screen system, audio recognition device, stylus, mouse, track ball, buttons, knobs, card reader, and/or switch, that accomplishes this function. In the illustrated embodiment, a knob and keypad 50 are used as an input device.

Control unit 42 is any suitable device that can perform the functions discussed above with respect to pressure generating system 32 and the input/output functions of interactive system 34. It is to be understood, however, that these two functions can be carried out by separate control devices associated with the respective pressure generating and interactive systems 32 and 34. Control unit 42 can also include a suitable amount of memory for storing information necessary to carry out these functions, such as sufficient memory to store the indicia to present to the user and the responses thereto.

In the illustrated embodiment, interactive system 34 also includes a communication unit 52 and additional memory 54, both of which are optional in that they are not necessary to carry out the interactive function of interactive system 34. Communication unit 52 provides the interactive system with the capability of transmitting information to and/or receiving information from an external device. In addition, communication unit 52 allows the operating parameters of the therapy device to be monitored, controlled, or both from an external device. Communication unit 52 is any device, such as a modem, RS-232, ISDN or other connection or data transportation system that permits information to be provided to and output from the control unit.

Memory 54 functions as an extended memory, supplementing the memory that is provided in control unit 42. Memory 54 can be used to store, for example, additional tests to provide to the patient, an extended amount of results input from the patient and/or the scores associated with the results provided by the patient. This information is downloaded periodically, upon request via communication unit 52, or if the results of the tests are outside predetermined boundary criteria. For example, if the results of the test indicate that the patient's condition is worsening dramatically, the results of the test and an alarm, if desired, can be automatically provided by the interactive pressure support system to the remote location or locations.

The present invention also contemplates that the function of communication unit 52 and memory 54 can be combined into a single system. For example, a "smart card" that contains memory, commands, data or any combination thereof can be provided in communication with control unit 42. Such a card preferably inserts into a receiving port provided in the housing containing control unit 42 and allows data, such as the results of the tests and compliance data regarding the use of the therapy device gathered by the control unit, to be stored on the card. When desired, the card containing such data is physically removed from the housing and sent via mail to a management center that collects this data. The smart card can also be programmed with commands or instructions that can be downloaded to control unit 42. For example, the tests administered to the patient or the operating pressure of the therapy device, e.g., the CPAP, inspiratory positive airway pressure (IPAP), or expiratory positive airway pressure (EPAP), can be changed by the supervising caregiver simply by providing suitable commands in the smart card that change these parameters.

It can thus be appreciated that the present invention provides flexibility in the tests provided to the patient so that, if necessary, the test questions, information, or tasks to be completed or performed by the patient can be tailored to meet the specific needs of that patient and can be changed as the patient changes. Also, the collection, processing, analyzing, tabulating and distribution of the actual (raw) results of the test or the calculation, processing and distribution the information determined based on the results of the test (the test score) can be stored, analyzed and distributed as necessary in a streamlined, automated fashion with minimal burdens on the test administrator. In addition, the operating parameters of the therapy device can be controlled and altered to meet the specific needs of that patient as the patient's condition changes.

Although FIG. 1 illustrates pressure generating system 32 and interactive system 34 as being provided in the same housing, a further embodiment of the present invention contemplates that these two system are not provided in the same housing but share a common element that requires interactive system 34 to be used in conjunction with the pressure generating system 32. For example, display 48 and/or input device 50 can be provided on a remote device, such as a hand-held LCD device, that communicates either wirelessly or via hard wire with the control unit in the interactive pressure support system 30 contained in the housing. Furthermore, other components of the interactive system, such as communication unit 52 and memory 54, can be provided in a unit external to housing 46.

Figure 3:
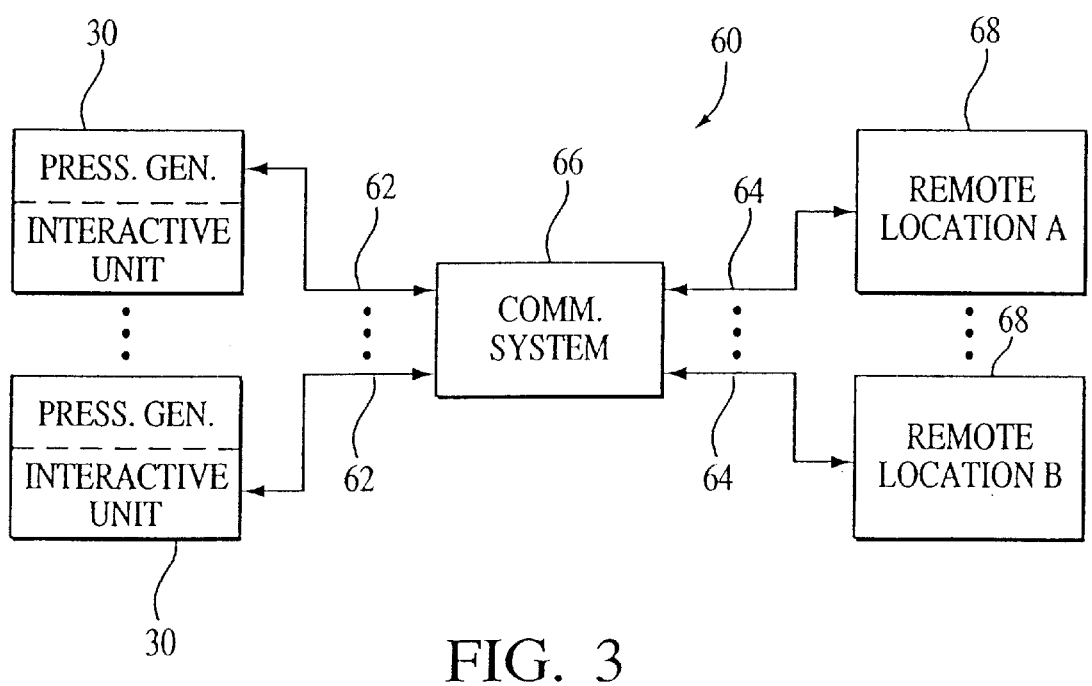
FIG. 3 is a schematic diagram of a communication network that includes the interactive pressure support system.

FIG. 3 is a schematic diagram of a communication network 60 that includes interactive pressure support system 30 of the present invention. In the illustrated network, a number of interactive pressure support systems 30 communicate via communication links 62 and 64 and communication system 66 to one or more remote locations 68. Communications links 62 and 64 can be hard wired or wireless so long as information is transmitted to and/or received from the interactive pressure support system 30 and/or remote locations. It is to be understood that the present invention contemplates that amplifiers, converters and adapters be provided where necessary to facilitate the transmission of data over the communications links. Communication system 66 is any communication network that transmits data from one location to another. For example, communication system 66 can be a conventional telephone or computer network with the interactive pressure support systems 30 communicating with remote locations 68 via modems, a satellite based system, a fiber optic/optical system, a microwave system or any combination thereof.

Remote locations 68 are any device capable of communicating with the interactive pressure support system 30. Typically, a remote location is a computer located at the care giver and/or test administrator. In an exemplary embodiment of the present invention, the user at the remote location downloads data from the interactive pressure support system 30 and/or base stations in communication system 66 that collect data from the interactive pressure support systems so that this information can be used to monitor the condition of the patient. It is to be understood, however, that the user at the interactive pressure support device can manually cause this data to be downloaded or the information can be downloaded automatically, such as at a set time each day, either due to programming in the interactive pressure support device or through an automatic query function in at a remote location. In addition, the data can be automatically downloaded by the interactive pressure support device if the results of the patient test are outside predetermined thresholds.

Figure 4:
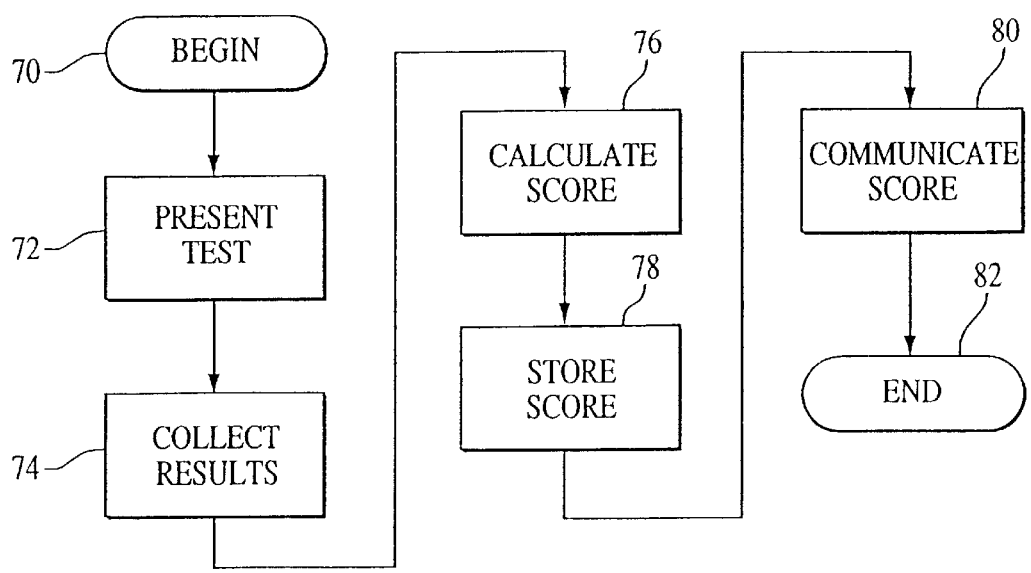
FIG. 4 is a flow chart illustrating one embodiment of the process carried out by the interactive pressure support system.

FIG. 4 is a flow chart illustrating one embodiment for the process carried out by the interactive pressure support system. The process begins in step 70 and can be initiated from a variety of sources. For example, the patient using interactive pressure support system 30 can manually request that a test be administered, the interactive pressure support system 30 can be programmed to administer a test periodically, or the user at the remote location can initiate the test as needed or periodically. Once initiated, the test is administered to the patient in step 72 using interactive system 34 as discussed above. In an exemplary embodiment of the present invention, the Epworth and/or Vigilance tests discussed above are administered to determine the patient's sleep propensity. During the testing process of step 72, the patient receives a question or other indicia and provides a response thereto.

The results of the question and/or the response to the indicia, such as reaction time and recognition accuracy, are collected in step 74. The present invention also contemplates storing data indicative of the time, either absolute or relative to a reference, when the test was taken. Steps 72 and 74 are repeated as necessary until the test is completed. The results of the test input by the patient using the input device are tabulated and, where appropriate, a test score is determined in step 76. Depending on the desired operation of the interactive system, the test score, the results of the test, and/or other data, such as the time the test was taken or information about the test, are stored in control unit 42 and/or memory 54 in step 78 for later retrieval and/or transmission to a remote location in step 80; or steps 78 and 80 are performed immediately upon completion of the test with the test results being sent immediately to a remote location, such as remote locations 68 or a processing system in communication system 66. The testing procedure terminates in step 82. Information about the time the test was taken is useful because it helps chart the progress of the therapy, especially when compared with the results of the test for a series of tests. Information about the test itself may include data identifying the test administered, if, for example, different types or levels of tests are to be presented. For example, during the treatment of a disorder, the patient may be given a sequence of tests over a period time that may or may not increase in difficulty. The data output by the present invention should include information indicating which test in the sequence of tests was administered to the patient.

It can thus be appreciated that the present invention provides a system that performs two functions: (1) it provides a treatment to the patient to correct a disorder suffered by the patient, such as a pressure support device to treat OSA, and (2) it provides an interactive function so that the caregiver can periodically monitor the effectiveness of the treatment by having the patient complete a test intended to measure the patient's condition using the same device used to treat the patient. Thus, the present invention minimizes the burden on the patient, caregiver and test administrators, increases the utility of conventional treatment devices, and improves the follow-up of patient treatment while reducing the cost of same.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An interactive pressure support system, comprising:
   (a) a pressure generating system adapted to provide a pressure therapy to a pulmonary system of a patient; and
   (b) an interactive system associated with the pressure generating system, the interactive system comprising:
      an output device programmed to provide a survey to a patient pertaining to such a patient's medical condition;
      an input device adapted to receive a response to the survey from such a patient; and
      a control unit programmed with the survey, wherein the control unit controls (1) operation of the output device to present the survey, and (2) collection of the response to the survey via the input device.

2. An interactive pressure support system according to claim 1, wherein the survey comprises a test that measures an effectiveness of the pressure therapy.

3. An interactive pressure support system according to claim 2, wherein the test is a series of questions that gage a patient's propensity for daytime sleepiness.

4. An interactive pressure support system according to claim 2, wherein the test measures at least one of reaction time and cognitive alertness of a patient.

5. An interactive pressure support system according to claim 1, wherein the control unit analyzes the response to the survey and determines a result based on the analysis, the result being a measure of a characteristic of a patient intended to be impacted by the pressure therapy.

6. An interactive pressure support system according to claim 5, wherein the interactive system further comprises a memory for storing at least one of the response to the survey and the result.

7. An interactive pressure support system according to claim 5, wherein the interactive system further comprises a communication unit adapted to communicate at least one of the survey, the response to the survey and the result with a remote location.

8. An interactive pressure support system according to claim 1, wherein the pressure generating system includes:
   a pressure generator that receives gas from at least one gas source and provides the gas to a patient at an elevated pressure;
   a breathing circuit having a first end operatively coupled to the pressure generator; and
   a patient interface device operatively coupled to a second end of the breathing circuit.

9. An interactive pressure support system according to claim 1, wherein the pressure generating system and the interactive system are associated with one another by being operatively coupled to a common housing.

10. An interactive pressure support system according to claim 1, wherein the interactive system further comprises a memory for storing the survey and the response to the survey.

11. An interactive pressure support system according to claim 1, wherein the interactive system also collects other information associated with at least one of the survey and the response to the survey.

12. An interactive pressure support system according to claim 11, wherein the other information includes at least one of (1) time information identifying at least one of (a) a test administration time indicating a time when the survey was presented to a user and (b) a test completion time indicating a time when the response to the survey was received from a user, and (2) identifying information identifying the survey provided to a user.

13. An interactive pressure support system, comprising:
   pressure generating means for generating a pressure therapy adapted to be provided to a pulmonary system of a patient; and
   patient interacting means, associated with the pressure generating means, for providing a survey to a patient pertaining to such a patient's medical condition and for receiving a response to the survey from a patient.

14. An interactive pressure support system according to claim 13, wherein the survey comprises a test that measures an effectiveness of the pressure therapy.

15. An interactive pressure support system according to claim 14, wherein the test is a series of questions that gage a patient's propensity for daytime sleepiness.

16. An interactive pressure support system according to claim 14, wherein the test measures at least one of reaction time and cognitive alertness of a patient.

17. An interactive pressure support system according to claim 13, wherein a patient interacting means analyzes the response to the survey and determines a result based on the analysis, the result being a measure of a characteristic of a patient intended to be impacted by the pressure therapy.

18. An interactive pressure support system according to claim 17, wherein a patient interacting means includes a communicating means for communicating at least one of the survey, the response to the survey and the result with a remote location.

19. An interactive pressure support system according to claim 13, wherein the pressure generating means includes:
   a pressure generator that receives gas from at least one gas source and provides the gas at an elevated pressure;
   a breathing circuit having a first end operatively coupled to the pressure generator; and
   a patient interface device operatively coupled to a second end of the breathing circuit.

20. An interactive pressure support system according to claim 13, wherein the pressure generating means and a patient interacting means are associated with one another by being operatively coupled to a common housing.

21. A communication network comprising:
   at least one interactive pressure support system, comprising:
      (a) a pressure generating system adapted to provide a pressure therapy to a pulmonary system of a patient; and
      (b) an interactive system associated with the pressure generating system, the interactive system comprising:
         an output device programmed to provide a survey to a patient pertaining to such a patient's medical condition,
         an input device adapted to receive a response to the survey from a patient, and
         a control unit programmed with the survey, wherein the control unit controls (1) operation of the output device to present the survey and (2) collection of the response to the survey via the input device;
   at least one remote location adapted to communicate with the at least one interactive pressure support system; and
   a communication system adapted to transmit information in at least one direction between the at least one interactive pressure support system and the at least one remote location.

* * * * *